(12) United States Patent
Carter

(10) Patent No.: US 6,209,144 B1
(45) Date of Patent: Apr. 3, 2001

(54) PROTECTIVE GARMENT

(76) Inventor: Eddie R. Carter, 478 Grand Oaks, Houston, TX (US) 77015

( * ) Notice: Subject to any disclaimer, the term of this patent is extended or adjusted under 35 U.S.C. 154(b) by 0 days.

(21) Appl. No.: 09/480,361

(22) Filed: Jan. 10, 2000

(51) Int. Cl.[7] .................................................. A62B 17/00
(52) U.S. Cl. .................................... 2/458; 2/81; 2/DIG. 1
(58) Field of Search .......................... 2/458, 457, DIG. 1, 2/2.16, 81, 93

(56) References Cited

U.S. PATENT DOCUMENTS

| | | | |
|---|---|---|---|
| 4,513,452 | * | 4/1985 | Rankin et al. ............................. 2/81 |
| 4,571,741 | * | 2/1986 | Guillaumot ................................. 2/8 |
| 5,127,896 | * | 7/1992 | de Gaston ......................... 2/2.14 X |
| 5,193,347 | * | 3/1993 | Apisdorf ................................ 62/3.7 |
| 5,245,993 | * | 9/1993 | McGrady et al. .............. 128/201.22 |
| 5,421,326 | * | 6/1995 | Rankin et al. .................. 128/201.19 |
| 5,438,707 | * | 8/1995 | Horn ....................................... 2/457 |
| 5,652,966 | * | 8/1997 | Reinert ................................... 2/457 |
| 5,774,902 | * | 7/1998 | Gehse ..................................... 2/458 |
| 5,970,519 | * | 10/1999 | Weber ....................................... 2/81 |

FOREIGN PATENT DOCUMENTS

| | | | |
|---|---|---|---|
| 1434956 | * | 11/1968 | (DE) ........................................ 2/458 |
| 1233851 | * | 5/1986 | (SU) ........................................ 2/458 |

* cited by examiner

Primary Examiner—Rodney M. Lindsey
(74) Attorney, Agent, or Firm—Marvin J. Marnock

(57) ABSTRACT

A protective garment (10) adapted to be worn by personnel in high temperature or otherwise harmful environments. Tile garment comprises a torso section 11 and depending on the wearer's needs and desires, arms (14), head (13) and leg sections (15) and readily attachable complementary portions for covering the face, hands and feet extremities. The garment is equipped with a supply of precooled and dehumidified ventilating gas or other coolant medium to be flowed over various body parts of the wearer. The coolant supply comprises one or more storage containers (20) carried about the waist. The coolant is supplied therefrom through a valve (25) to an inlet (41) in the suit. From the inlet, the coolant medium is distributed through flexible conduits (50) which include component distribution systems (55A, 55B, 57A, 57B, 61A, 61B) leading to the various body parts. The conduits are preferably attached to the lining of the suit and each provided along its length with holes (59) which are of increasing diameters in the direction away from the suit inlet to provide more uniform flow to a body area. Each component distribution system includes a thermostatic valve (81) or valve (61) controlled by a thermocouple (60) fixed at a location in the distribution zone such as at the ankles, wrists, or waist of the wearer whereby the valve acts to control coolant flow to a particular body area in order to maintain the surface temperature of the particular body area in a narrow range about 72° to 76°. The garment also includes sensors for monitoring and signalling physiological signs and providing other information as to the location, physical condition and identity of the garment wearer and an electrical communications system for transmitting such information to a remote base station and for receiving information therefrom.

27 Claims, 13 Drawing Sheets

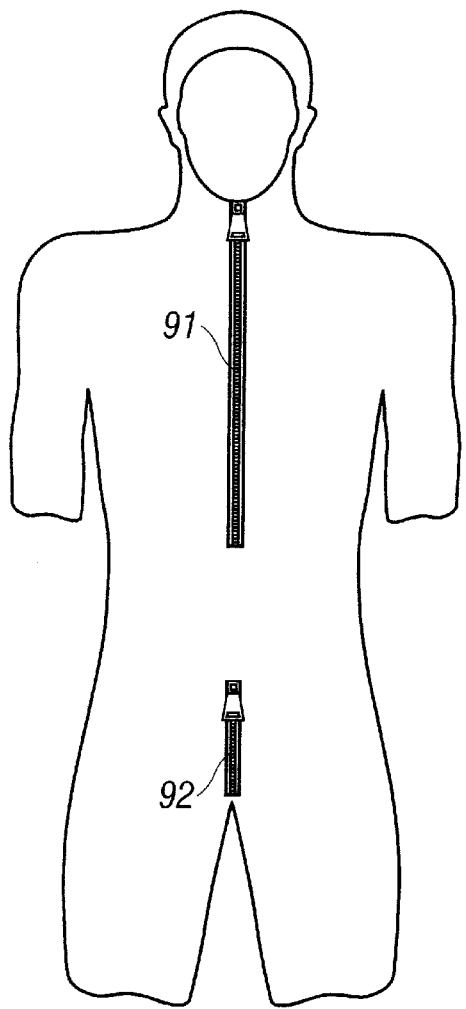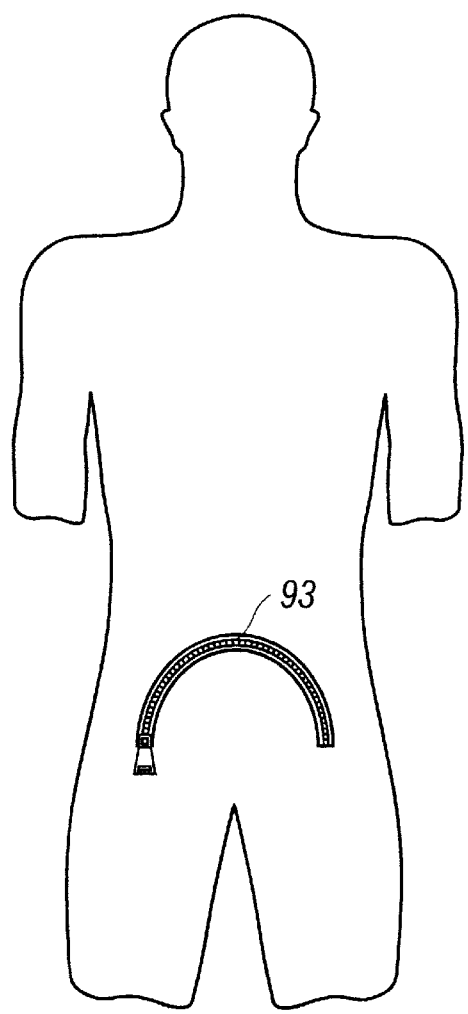
*FIG. 10A*  *FIG. 10B*

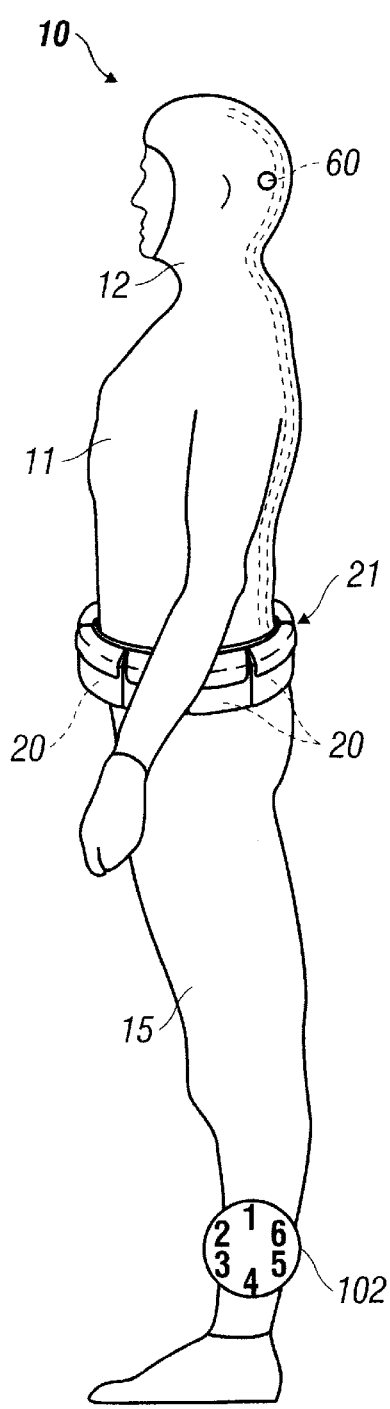
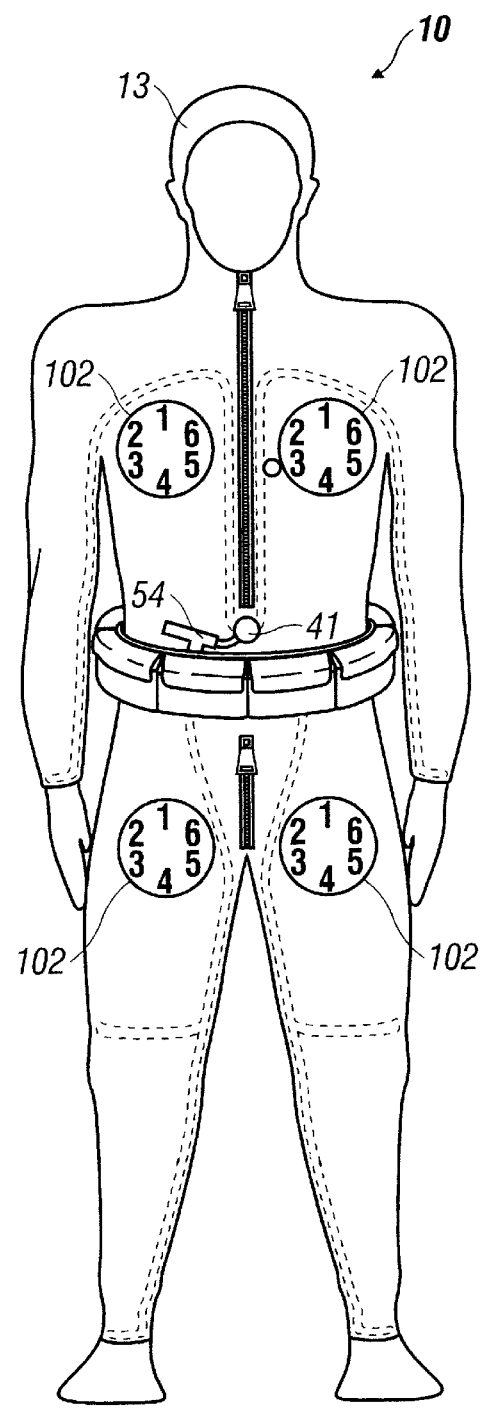
FIG. 13  FIG. 14

LOCAL SYSTEM

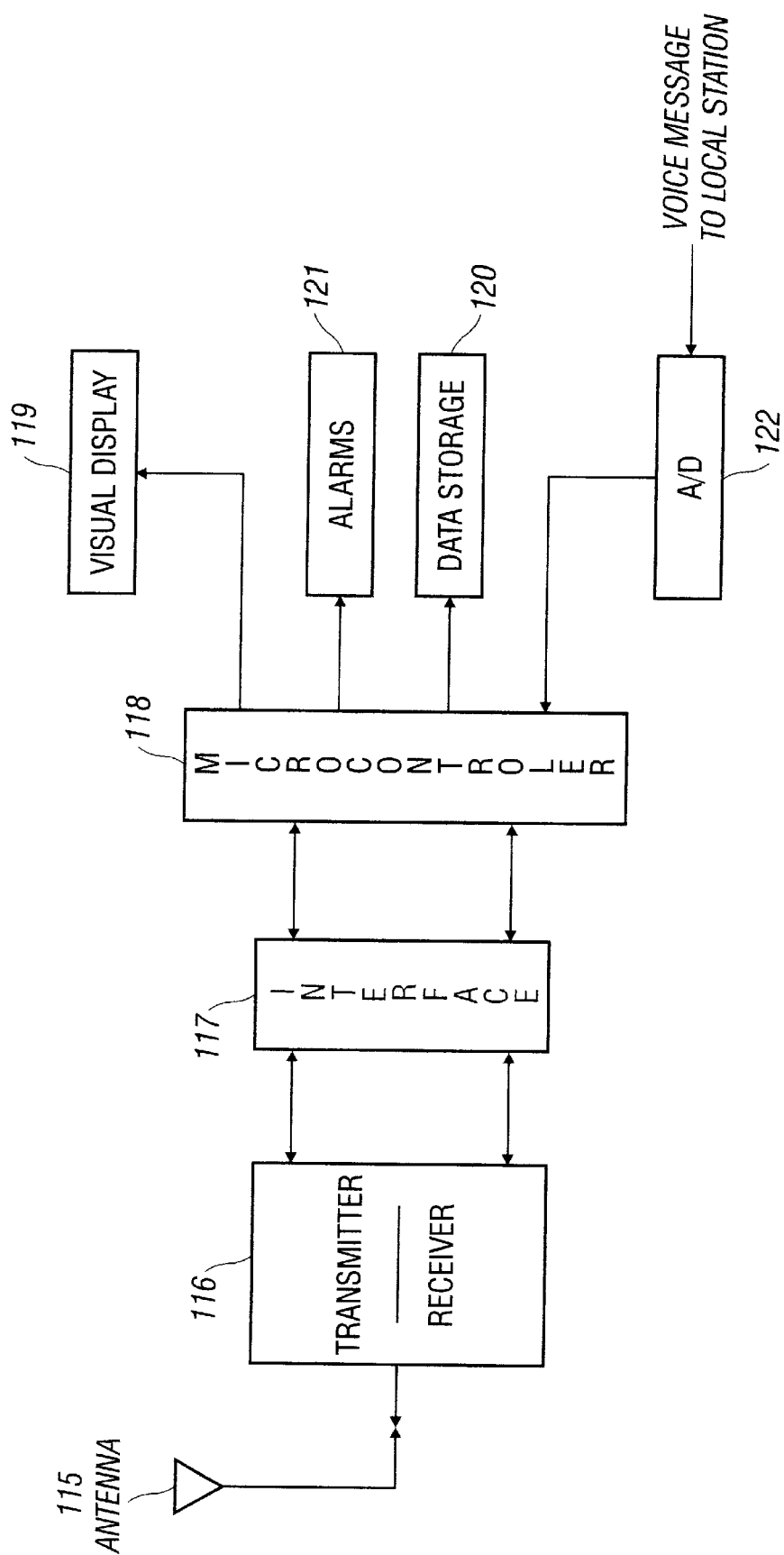
BASE STATION SYSTEM *FIG. 15B*

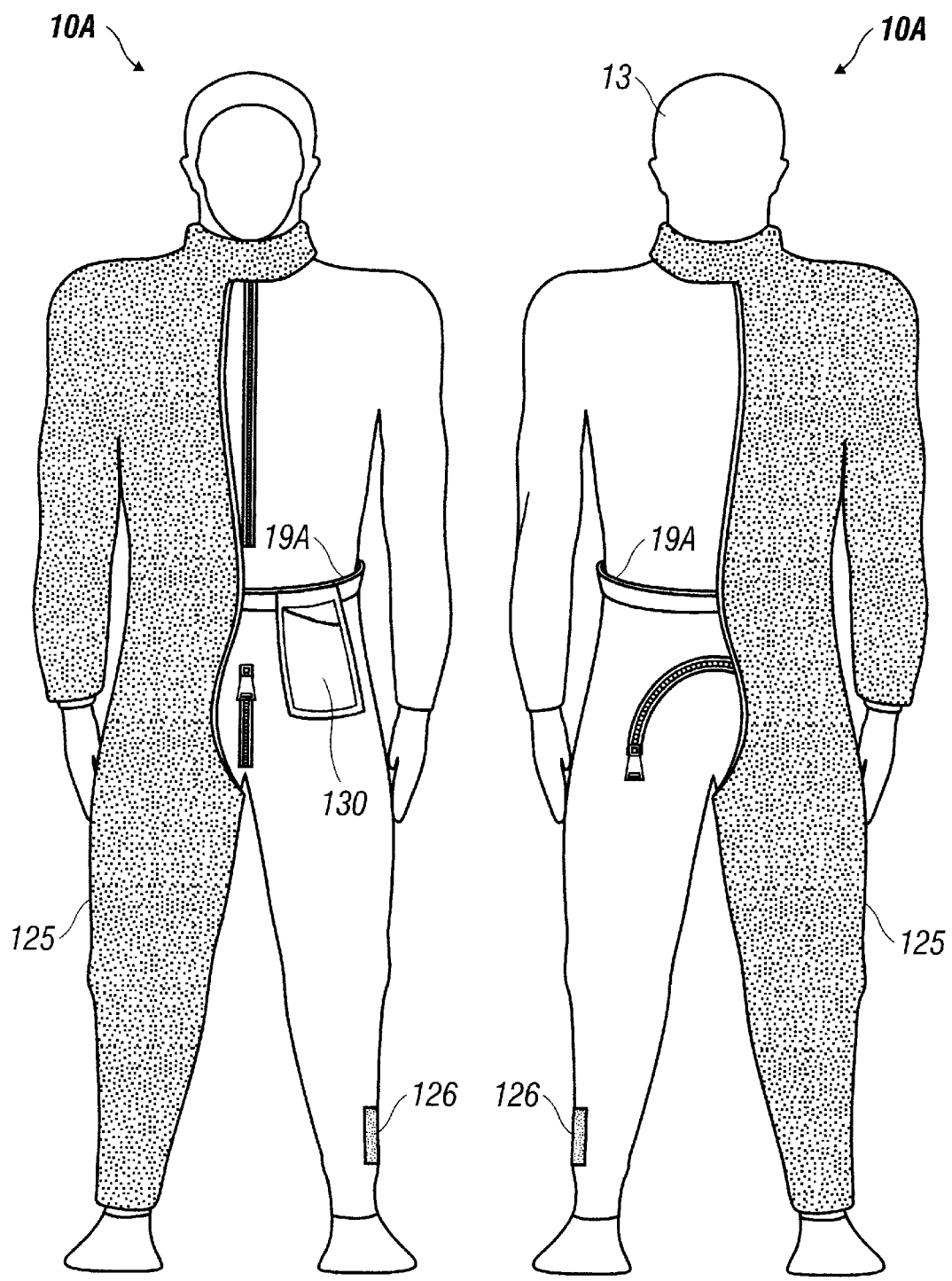
FIG. 16A  FIG. 16B

# PROTECTIVE GARMENT

FIELD OF THE INVENTION

The invention relates to a protective garment which is specially adapted to provide cooling for the body of a wearer and more particularly to a protective garment which is suitable for wear under harsh environmental conditions, includes means for distributing a cooling fluid, such as water or gas, over the wearer's body and selectively controlling its distribution so as to maintain or adjust the temperature for different areas of the wearer's body, and is equipped with devices for transmitting signal indications of the physical condition, location and identity of the garment-wearer and for receiving signals which are relevant thereto.

BACKGROUND OF THE INVENTION

Protective garments which are adapted to protect and control the temperature of a wearer's body are frequently a necessity for persons when in harsh environments, as for example, oil field workers in the desert or other high temperature climates, fire fighters when fighting a fire, and construction craftsmen such as pipe fitters, welders, and millwrights who oftentimes must work in enclosed vessels or similarly confining spaces where the temperature may exceed 100° F. Suits made of material such as Nomex have been devised for those who work in hostile atmospheres 'such as in chemical plants and petrochemical refineries. While a variety of such garments have been devised, all are lacking in one or more aspects which either endanger the garment wearer or add to his discomfort. A typical problem is an inability of the garment to maintain temperature in healthful and tolerable ranges about different areas of the wearer's body. Another problem is an inability to control the amount of moisture in the cooling fluid which therefore complicates system operation and adds to the wearer's discomfort. In addition, the protective garments in the prior art typically require cumbersome backpacks ar supporting paraphernalia which can seriously impede the activity of the wearer and which typically lack any means whereby information as to the wearer's physical condition, identity or location can be ascertained by a distant observer.

SUMMARY OF THE INVENTION

The protective garment of the present invention is designed to provide improvement in the art of ventilating environmental suits of the type adapted to be worn by personnel in high temperature, corrosive or otherwise harmful environments. The garment structure of the invention comprises sections for at least covering the torso of the wearer and the wearer's arms, legs and head as may be desired. In addition, depending on the wearer's needs and desires, the face, hands and feet extremities can also be covered by readily attachable complementary portions to the garment. The garment suit material is elastic and durable, and preferably impervious to the cooling fluid, particularly when the cooling medium is a liquid. The garment includes means for supplying and distributing a precooled and dehumidified ventilating gas to flow over the various body parts of the wearer. A supply of the coolant medium is carried on the wearer's suit or torso and the coolant is supplied therefrom to an inlet provided in the suit. From the inlet, the coolant is distributed through a system of conduits, which includes component distribution systems leading to the various body parts. The conduits are preferably attached to the interior lining of the suit and each provided with holes along its length for communicating the coolant medium to the interior of the suit for application to the wearer's body. Each component distribution system includes a valve controlled in its operation to increase or decrease coolant flow to a particular body area in order to maintain the surface temperature of the particular body area in a narrow range about 72° F. to 76° F. The garment may also be provided with sensors for monitoring and signalling indications of the physical condition, identity and location of the wearer.

BRIEF DESCRIPTION OF THE DRAWINGS

FIG. 10A is a schematic fragmentary view of the front of one embodiment of the invention showing provision of KEVLAR zippers in the front of the garment;

FIG. 10B is a schematic fragmentary dorsal view of the garment of FIG. 10A showing provision of a KEVLAR zipper;

FIG. 13 is a view of the garment wearer which shows a sensor probe located on the suit just above the ankle of the garment wearer;

FIG. 14 is a front view of the garment wearer which shows sensor probes locate adjacent the wearer's chest and also sensor probes positioned adjacent the right and left thigh.

FIG. 15B is a schematic diagram of a communications network located at a base station, and which is adapted to receive and process signals from one or more garment-wearers of the invention and to transmit signals to said garment wearer;

FIG. 16A is a front view of a person wearing the protective garment of the invention and with coveralls superimposed thereover and a KEVLAR belt with a holster-like attachment used in lieu of the belt of FIG. 3 and wherein a portion of the coveralls is omitted for purposes of illustration; and FIG. 16B is a back view of the garment wearer of FIG. 16A, showing only a portion of the coveralls and the protective garment of the invention.

DETAILED DESCRIPTION OF THE INVENTION

Figure 1:
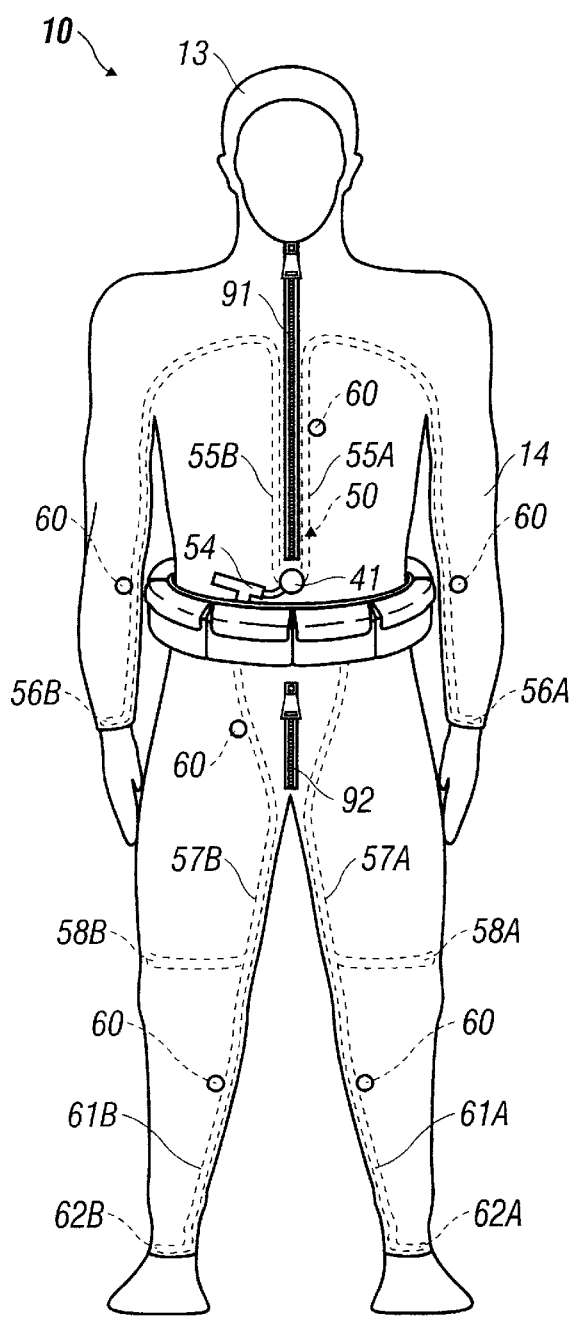
FIG. 1 is a front view of the protective garment of the present invention showing the garment as worn on a person and a portion of the conduit distribution system which is fastened thereto.
Figure 2:
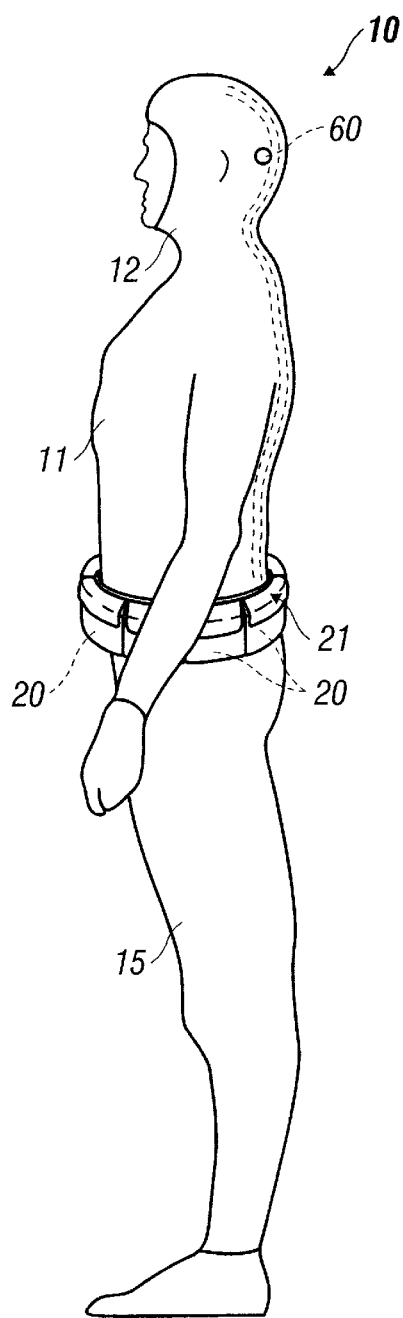
FIG. 2 is a side view of the garment shown in FIG. 1.

Referring more particularly to the drawings, there is shown in FIGS. 1 and 2 a body enveloping garment 10 made of an elastic, flexible material 10A such as Neoprene, or Spandex or the like. For use by firemen, the garment material would be of fire-resistant material such as Nomex. The garment is shown as it appears when fitted on a person who has need of a relatively uncumbersome protective garment. The garment comprises a torso section 11 with a neck portion 12 to which is attached a hood portion 13 for covering the head of a person when wearing the suit. The face is shown uncovered but if the wearer desires, a complementary face mask could be provided which is readily attachable to the garment 10. The protective garment or suit 10 also comprises arm portions 14 which terminate at the wrists and leg portions 15 which terminate at the ankles or, if desired, in boots which completely enclose the feet of the wearer.

Figure 3:
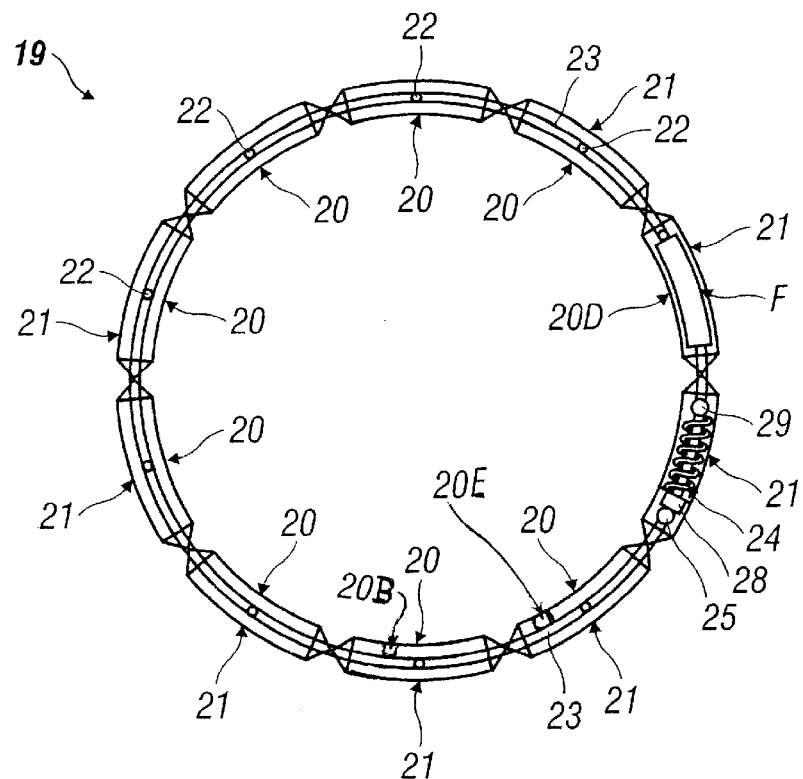
FIG. 3 is a top plan view showing a plurality of containers as they are arranged and attached as a belt about the waist of the garment of FIG. 1.
Figure 4:
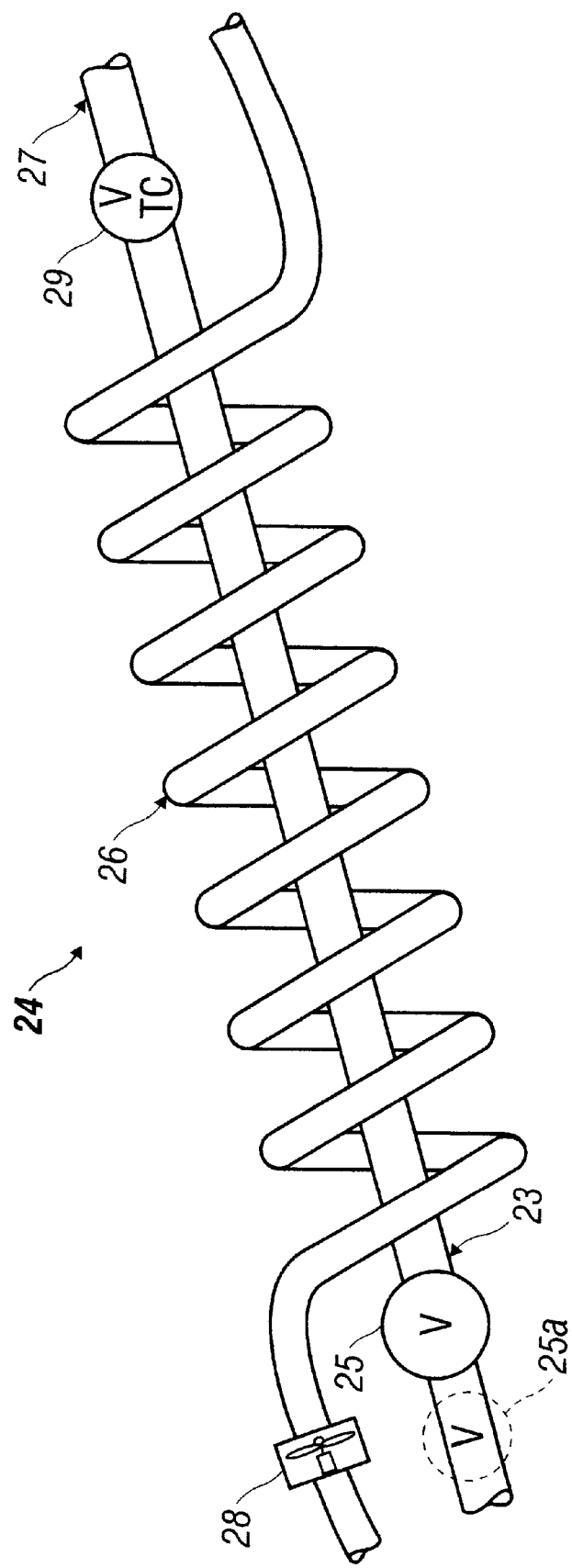
FIG. 4 is an enlarged schematic view of a heat exchanger which is adapted to receive a coolant gas from the coolant containers of FIG. 3.

To accomplish a principal purpose of the protective garment 10, which is to maintain the body temperature of the garment wearer at a comfortable and safe level at the wearer's body extremities and important body areas, the garment is provided with a supply of a ventilating coolant medium and means for distributing the coolant medium to the various body areas in a controlled manner. The maintenance of the desired temperature may be facilitated by the use of carbon dioxide, nitrogen or any inert gas such as argon as the coolant medium, preferably in compressed form but alternatively in liquid form, particularly where long use applications are expected. The coolant medium is stored in a plurality of canister-like containers 20 which are mounted in pockets 21 of KEVLAR material arranged in encircling relation on a KEVLAR belt adapted to be fastened about the waist of the suit. Each container is arcuate in shape with a curvature which conforms generally to that of the waist of the wearer as shown in FIGS. 1–3, such that the coolant containers 20 do not constitute a major impediment to the mobility of the garment wearer as would a back-pack on occasions where the wearer might be required to pass through a narrow opening. The belt 19, shown in FIG. 3, may be provided with a connecter buckle (not shown) or custom designed for the wearer. It is also to be noted that the containers are substantially enclosed by KEVLAR material in pockets provided on the KEVLAR belt which constitutes a safety feature in that the canisters are typically containing a coolant medium under very high pressure. The outlet conduits 22 from each of the storage containers 20 merge in a single flexible conduit 23 which connects through a manually controlled valve 25 to a heat exchanger 24 as shown in FIG. 4. As a safety feature, a pressure relief valve 25a may be included. When the garment wearer turns the valve 25 to its open condition, the cooling medium which has been pre-cooled to a very low sub-freezing temperature is delivered to the heat exchanger 24, shown in FIG. 4. A small battery powered fan 28 is provided to force the flow of ambient air through a flexible pipe 26 coiled about the coolant conduit 23. Preferably, the heat exchanger and fan with battery are placed in one of the belt pockets 21 left open at the top, such that the fan switch is readily accessible and can be switched on or off by the garment wearer as he so desires or as regulated by a microcontroller.

A thermostatic valve 29 which is installed in the outlet end 27 of the heat exchanger, is designed to open when the surface temperature of the wearer's body reaches approximately 76° F.

Figure 5A:
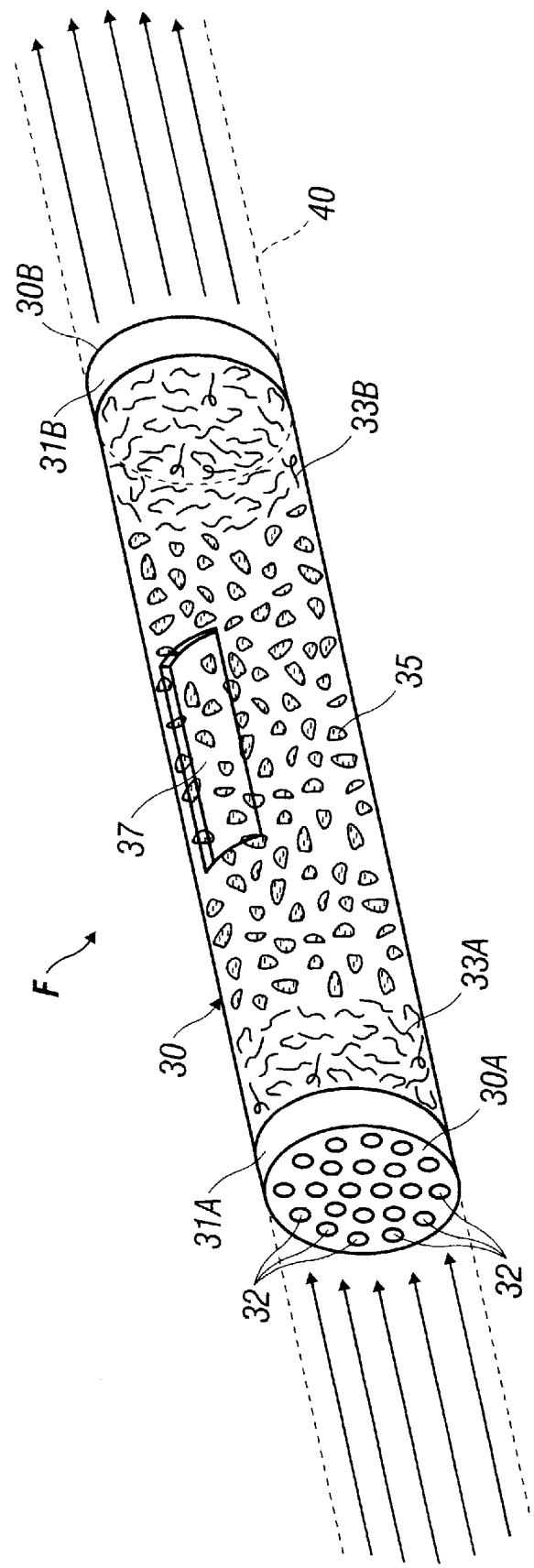
FIG. 5A is an enlarged perspective view of a moisture filter which receives coolant from the heat exchanger shown in FIG. 4 before its delivery to the conduit system shown in FIG. 6.
Figure 5B:
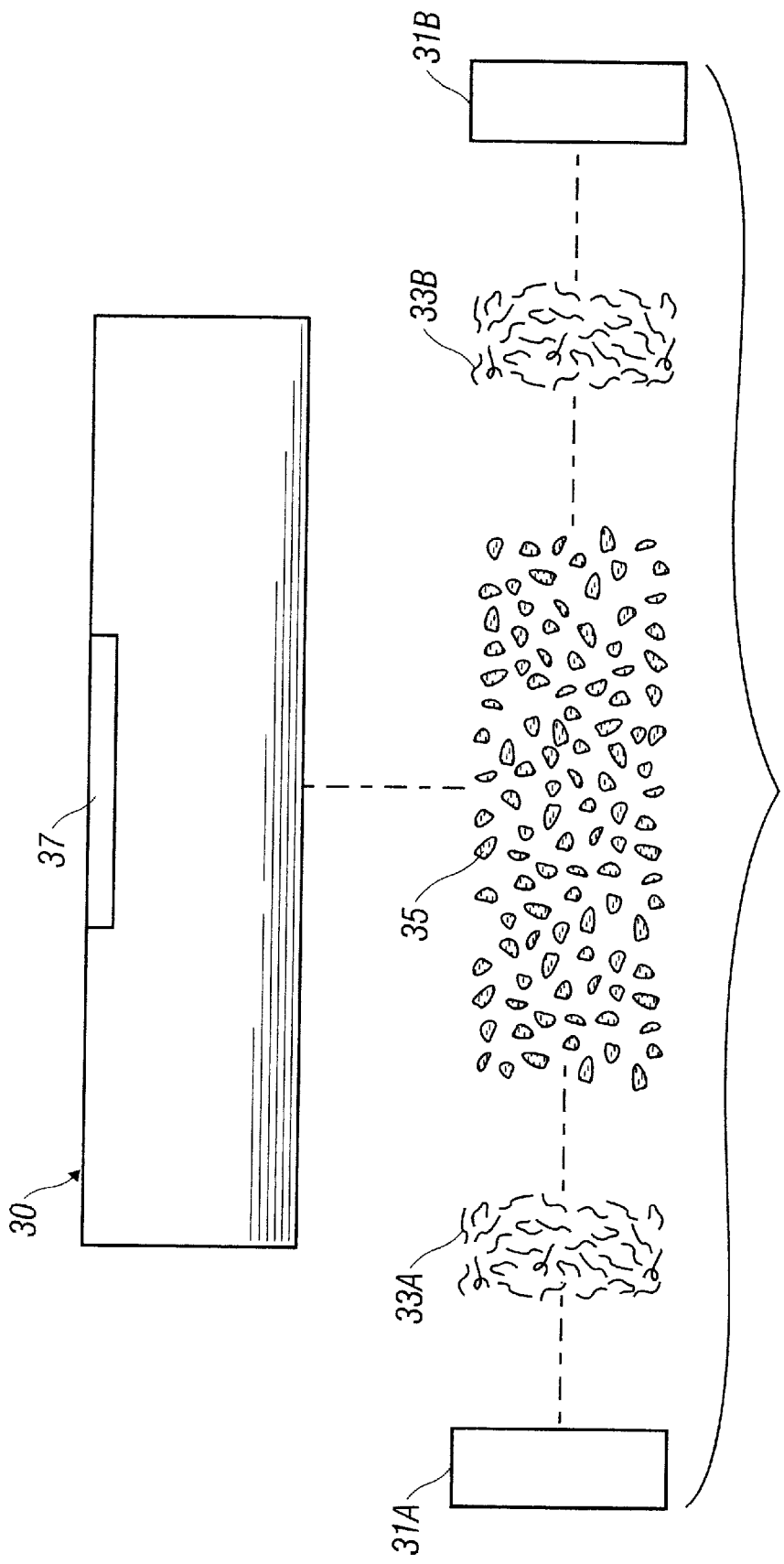
FIG. 5B is an exploded view of the component parts of the filter of FIG. 5A.

The outlet 27 of the heat exchanger delivers the cooled medium from the pipe 23 to a filter "F" shown in FIGS. 5A and 5B, which serves to purify and demoisturize the input cooling media. The filter F includes an elongate tubular housing 30 of circular radial cross section and provided at each end 30A, 30B with a transverse plastic wafer 31A, 31B which has perforations 32 for allowing passage of the coolant through the filter. At each end, the filter also includes a medium of glass wool, "angel hair", or carbon black positioned to abut the plastic wafer at each end of the filter which serve to collect contaminant, dust particles, or hazardous organic materials in the coolant media. Between the two glass wool layers 33A, 33B, the filter is filled with moisture removing material 35 of anhydrous calcium sulfate, available commercially as Dri-Rite. Such moisture removal material is "blue" in color in its dry state and turns "pink" as water is filtered out of the coolant media and absorbed therein. A transparent window 37 in the filter housing 30 mounted in one of the pockets 21 allows the suit wearer to observe the color change and provide for its removal and replacement as necessary.

In operation, when the valve 25 is opened by the garment wearer, and coolant medium is delivered to the heat exchanger and filter, dehumidified ventilating gas is supplied from the filter F through a flexible conduit 40 to a manifold 54 connected to the gas inlet 41 of the environmental suit 10 and thereby flows through the suit conduit distribution system over the various body parts.

Figure 6:
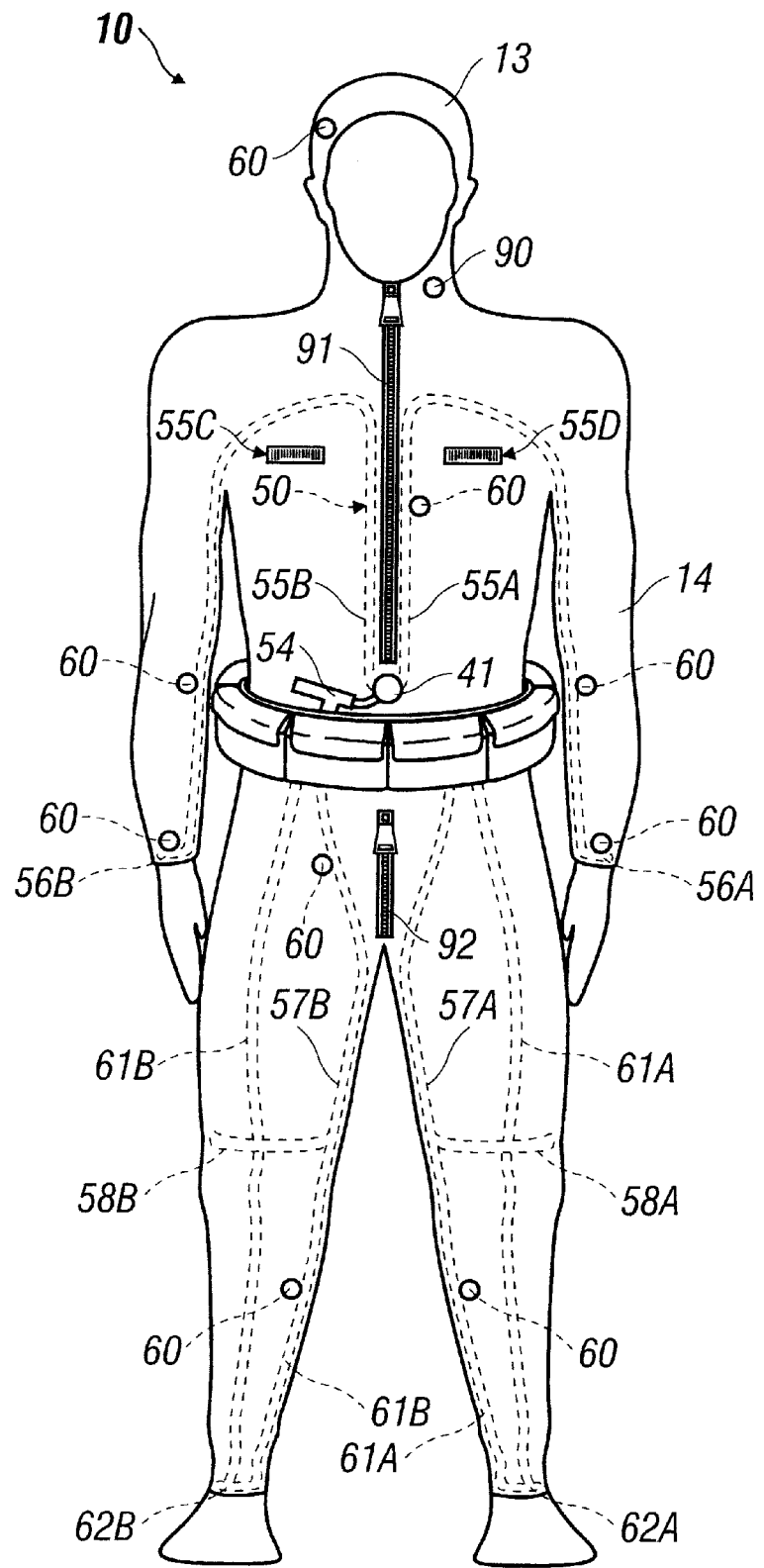
FIG. 6 is a front view of the garment of FIG. 1 showing the conduit system for distribution of a coolant medium over specific areas of the garment wearer's body and with bar code strips affixed to the garment exterior.
Figure 8:
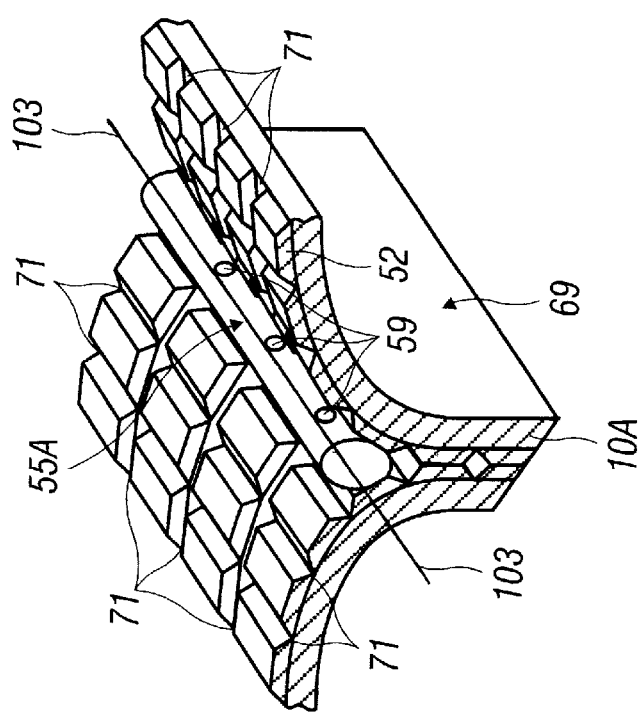
FIG. 8 is a fragmentary view of a seam of the protective garment of the invention showing the location of a conduit as it is attached to the interior of the garment and which is a part of the coolant distribution system for the garment.

The conduits in the distribution system 50, as shown in FIG. 6, are preferably of flexible plastic or elastomeric material and are adhered to seams in the suit material 10A, as shown in FIG. 8, by stitching 52 or otherwise.

Figure 7:
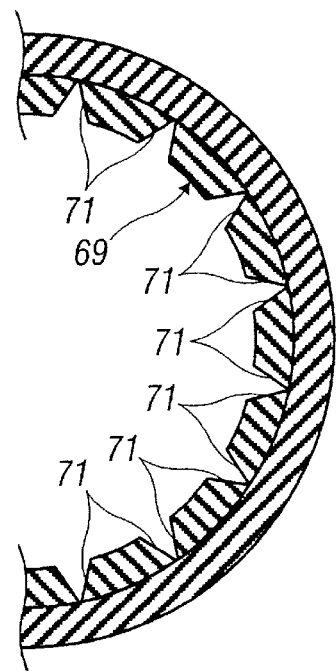
FIG. 7 is a fragmentary section view of the inner lining of the garment and showing the grooves provided therein which cooperate with the conduit system for distribution of coolant.

The conduit distribution system 50 includes the central manifold 54 located near the waist and a plurality of conduits which extend from the manifold to various parts of the protective garment to deliver coolant media to selected surface areas of the wearer's body. Each of the conduits such as conduit 55A is provided with small holes 59 (see FIG. 8) along its length which face toward the inner lining 69 of the garment and are positioned to communicate with grooves 71 provided in the inner face of the lining 69 in a criss-cross pattern of grooves such as shown in FIGS. 7 and 8. The lining 69 is preferably of a soft flexible water-resistant material such as neoprene rubber or a plastic. Also, to equalize the amount of coolant flow to the inner facing area between the garment lining and the wearer's skin at the various body areas, the holes 59 in the conduits are provided with increasingly larger diameters proportionate to their distance from the central manifold 54 thereby compensating for pressure drop as coolant moves through a conduit.

As best shown in FIG. 6, a pair of branch conduits 55A, 55B extend from the central manifold 54 upward along the middle of the chest section of the suit, and then, in opposite directions, laterally across the upper part of the chest and down along the arms to the wrists. As shown in FIG. 6, the branch 55A extends long the inner side of the left arm to end in a ring-like duct 56A which encircles the left wrist. Similarly, the branch 55B extends along the inner side of the right arm and terminates in a ring-like duct 56B which encircles the right wrist. The ducts 56A and 56B are each provided along their length with a plurality of holes which are selectively positioned to directly communicate the coolant to grooves 71 in the garment lining. In addition, a pair of bar code strips 55C, 55D are affixed to the front chest portion of the garment for identification purposes to be hereinafter explained.

Also, as shown in FIG. 6 a second pair of conduit branches 57A, 57B extend from the manifold 54, with the branch 57A extending downwardly along the left leg to a ring-like duct 58A which encircles the left leg just above the knee and the branch 57B extending downward along the right leg to a ring-like duct 58B which encircles the right leg just above the knee.

A third pair of branch conduits 61A, 61B extend from the manifold 54 along the inside of the left and right legs, respectively, with branch 61A communicating with a ring-like duct 62A about the left ankle and branch 61B communicating with a ring-like duct 62B about the right ankle.

Figure 9A:
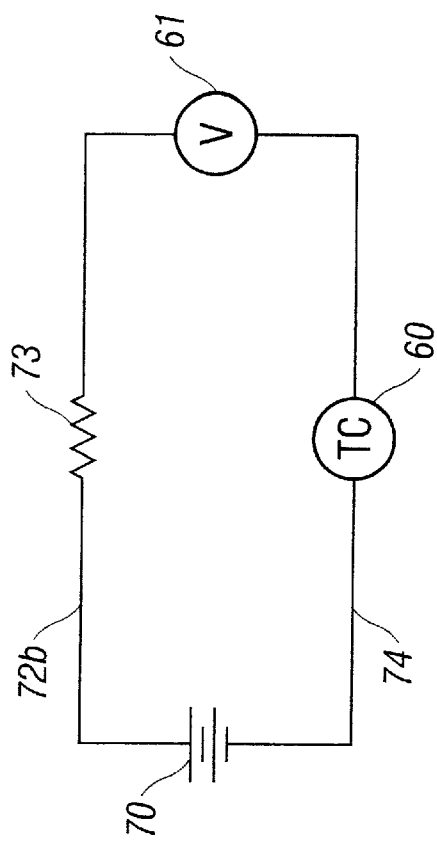
FIG. 9A is a schematic electrical circuit diagram of a thermostatically controlled system for controlling flow of a coolant medium to a particular area of the garment wearer's body.

The cooling system is also provided with thermocouples 60, each of which is strategically located in an associated body area and is a component in a battery-powered temperature control system as shown in FIG. 9A. The number of thermocouples employed corresponds with the number of body areas selected for temperature control, and while seven are shown in the embodiment of the invention described herein it is to be appreciated that the number may be greater or lesser than seven. Each thermocouple 60 functions as a thermostat which controls a solenoid valve 61 operatively associated therewith to open the valve when the surface body temperature meets or exceeds 76° F. and to close the valve 61 when the surface body temperature drops below 72° F. to thereby increase or decrease the flow in its associated coolant distribution system and thereby maintain the entire body surface temperature area in a relatively narrow comfort range about 74° F. plus or minus 1° F. The preferred thermocouple for each control system is a commercially available "J" type thermocouple and the preferred conductor materials are platinum, gold, nickel, and silver.

One thermocouple 60 is located above the waist and controls its associated valve 61 for maintaining coolant flow and body temperature in the wearer's upper torso, chest and back area. A thermocouple 60 is also mounted adjacent each ankle for monitoring and controlling the temperature about each of the wearer's lower legs by its control of its associated valve 61. A thermocouple 60 fastened to the suit interior near the wearer's crotch monitors and controls the surface temperature about the wearer's crotch and upper thighs. A thermocouple 60 mounted in the hood of the suit 10 monitors head and neck temperature, and thermocouples 60 on the forearms adjacent each wrist control temperature of the lower arms.

In FIG. 9A, there is shown a schematic electrical diagram which illustrates a control system for automatically controlling the flow of coolant to a particular body area, such as the upper torso. The thermocouple 60 is in effect a thermostatic switch which is coupled at one end by a conductor 74 to one terminal of a battery 70 and at its other end by a conductor 72a to the solenoid of a solenoid valve 61 which connects to the other terminal of the battery 70 through a resistor 73 and a conductor 72b. The thermocouple 60 closes the circuit whenever the temperature in the torso area reaches 76° and thereby opens the valve 61 to distribute coolant to the upper torso area. When the temperature reaches 72° F., the thermocouple opens the circuit, closing the valve 61 and cutting off the coolant flow to the upper torso area.

The other six body areas are similarly controlled by identical thermocouple and solenoid valve circuits. Preferably, the conductors from each thermocouple or thermostatic valve extend along a conduit and lead to its associated battery and circuit resistor which is also carried near the waist, preferably in one of the pockets 21. However, it is to be understood that the number of body areas to be controlled by thermocouples need not be limited to six but may be greater or lesser in number.

Figure 9B:
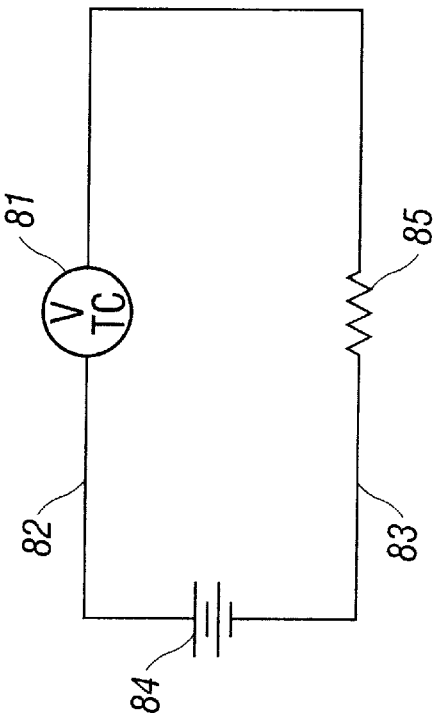
FIG. 9B is a schematic electrical circuit diagram of an alternative embodiment of the control system for thermostatically controlling the flow of coolant to a particular area of the garment wearer's body

An alternative electrical system is shown in FIG. 9B, wherein a thermostatic valve 81 is connected by conductors 82,83 to the opposite terminals of a battery 84 in a circuit in which the conductor 83 includes a resistor 85. The thermostatic valve 81 serves as a substitute for a thermocouple 60 and its associated solenoid valve 61. Such a thermostatic valve 61 must also be placed in its associated body control area.

When designed for use by firemen, the protective garment of the invention may also be provided with a temperature sensor 90 such as a bimetallic strip sensor of conventional type sensor which may be fastened to the neck collar area of the outer fire suit as shown in FIG. 6 and equipped to provide an audible alarm when an extremely high temperature environment is approached. As an alternative, in lieu of the bimetallic strip sensor, an infra-red detector for detecting "hot spots" may be mounted on the outer fire suit and operatively connected with an audible alarm on the sensor which can be heard by the garment wearer. Such an apparatus is shown in U.S. Pat. No. 5,781,215 (FIG. 3A) and incorporated herein by reference.

It is also desirable that a protective garment permit easy entry and removal for the wearer as well as allow the wearer to eliminate body wastes as may be necessary without requiring removal of the garment. For these purposes a KEVLAR zipper 91 is provided in the front of the garment to extend downward from the neckline opening to approximately the waistline as shown in FIG. 10A. To accommodate the wearer's need for elimination of body waste, a second zipper 92 is provided below the waist in the front of the garment and a third zipper 93 is provided in the rear of the garment below the waistline as shown in FIG. 10B.

Figure 11:
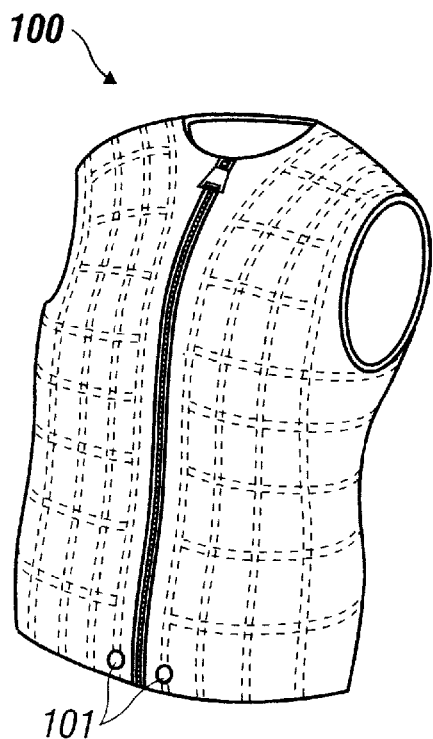
FIG. 11 shows in perspective view another embodiment of the invention wherein the protective garment of the invention is designed as a vest.

It is also to be noted that the protective garment 10 as described herein is comprised of arms, legs, head and torso sections of the wearer. However, for some environments it may be only necessary or desirable to cover only a part of the wearer's body. Another embodiment of the invention as shown in FIG. 11 is designed as a vest 100 which protects only the upper torso. Such a garment might also be provided with arm sections and a hood if desired. The garment 100 would be provided with an inlet or inlets 101 or inlets which can be connected in communication with the outlet of a manifold, such as the manifold 54, to receive the flow of coolant medium from canisters 20 carried on a KEVLAR waist belt, and wherein the coolant is warmed by a heat exchanger and filtered as described for the garment 10.

It is also sometimes of great importance to those who need to monitor the activities of the garment wearer, such as a fire-fighter, to receive current information as to his physical condition, location and safety, e.g., whether or not the fire-fighter is immobile, unconscious or under severe stress. Accordingly, the protective garment of the present invention is designed to be provided with a motion sensor 20C, such as described in U.S. Pat. No. 4,292,630, U.S. Pat. No. 4,110,741 (FIG. 1 thereof) or U.S. Pat. No. 5,751,215 and which typically include means for signalling an alarm, and also equipped with other sensors to provide information as to the wearer's vital physiological signs, such as pulse rate, respiration rate, blood oxygen saturation, intravascular volume status, and the body core temperature—the danger zone of which is near 105° F. The sensor responses are converted to electrical signals by appropriate transducers in conventional manner, then multiplexed, and transmitted by an antenna on the garment to a remote receiver station where they are demultiplexed and microprocessed for recording and display. Such an electrical system is adaptable to being incorporated in the garment 10 and mounted in a pocket 21 or a special holster-like pocket suspended on the belt 10.

Preferably, the suit further includes a "down fire-fighter" audible alarm circuit. The alarm circuit includes a motion sensor means 20C for sensing inertial forces, such as at least one accelerometer or one liquid throw switch, such as a mercury switch, and is structured to enable the audible tone of the alarm device, whenever the device is in the operational mode but is not moving. This capability is important when a fire-fighter is "down", e.g., unconscious within a burning building. Another fire-fighter within the sound range of the alarm is then able to locate the unconscious fire-fighter and rescue him. Also, the "base" or "mini-base" monitors will be immediately informed as to the downed fire-fighter's condition by means of the aforesaid communications system. Accordingly, a "Personnel Monitoring Man-Down Alarm System", such as disclosed in U.S. Pat. No. 5,045,839 or a "down fire-fighter" alarm as disclosed in U.S. Pat. No. 5,751,215, and incorporated herein by reference, may be incorporated into the garment of the present invention.

Filtering or interfering detectable input signals can be applied in the event, for example, where there is need of detection of motion, the critical factor is the need to be able to differentiate between motion and lack of motion. For instance, should a fire-fighter become unconscious near a vibrating piece of machinery, it then becomes necessary to differentiate between the vibration of the machinery and the motion or non-motion of the injured fire-fighter.

If the garment-wearer is motionless for a pre-determined period of time, such as 20 seconds, for example, the remote personnel unit will emit a low-level pulsating pre-alarm tone to warn the user that the motion sensor is about to transmit an alert alarm which will be received by the base station's transceiver. The pre-alarm tone can be stopped and the timing cycle re-set to zero by a gentle movement of the motion sensor radio transmitter or transceiver. If the user is motionless for another predetermined period of time, i.e. for a total of thirty seconds (10 seconds beyond the onset of the pre-alarm tone), the remote personnel unit will generate transmission.

Further, where there may be several fire-fighters or other workers active in hostile environment settings, it may be important to provide a means, an electronic procedure, to "keep records" as to "who" and "how many" workers are actively performing in the particular setting. Accordingly, each garment will include a crystal resonator, self-excited by physical motion, for transmitting a radio signal at a frequency assigned to a particular worker, which frequency will differ from those assigned to every other worker. The transmitted information will then be processed and recorded at a "base" or "mini-base" receiving station at a remote location. A patient ID system which transmits identifying signals is disclosed in U.S. Pat. No. 4,835,372 and incorporated herein by reference.

Figure 15A:
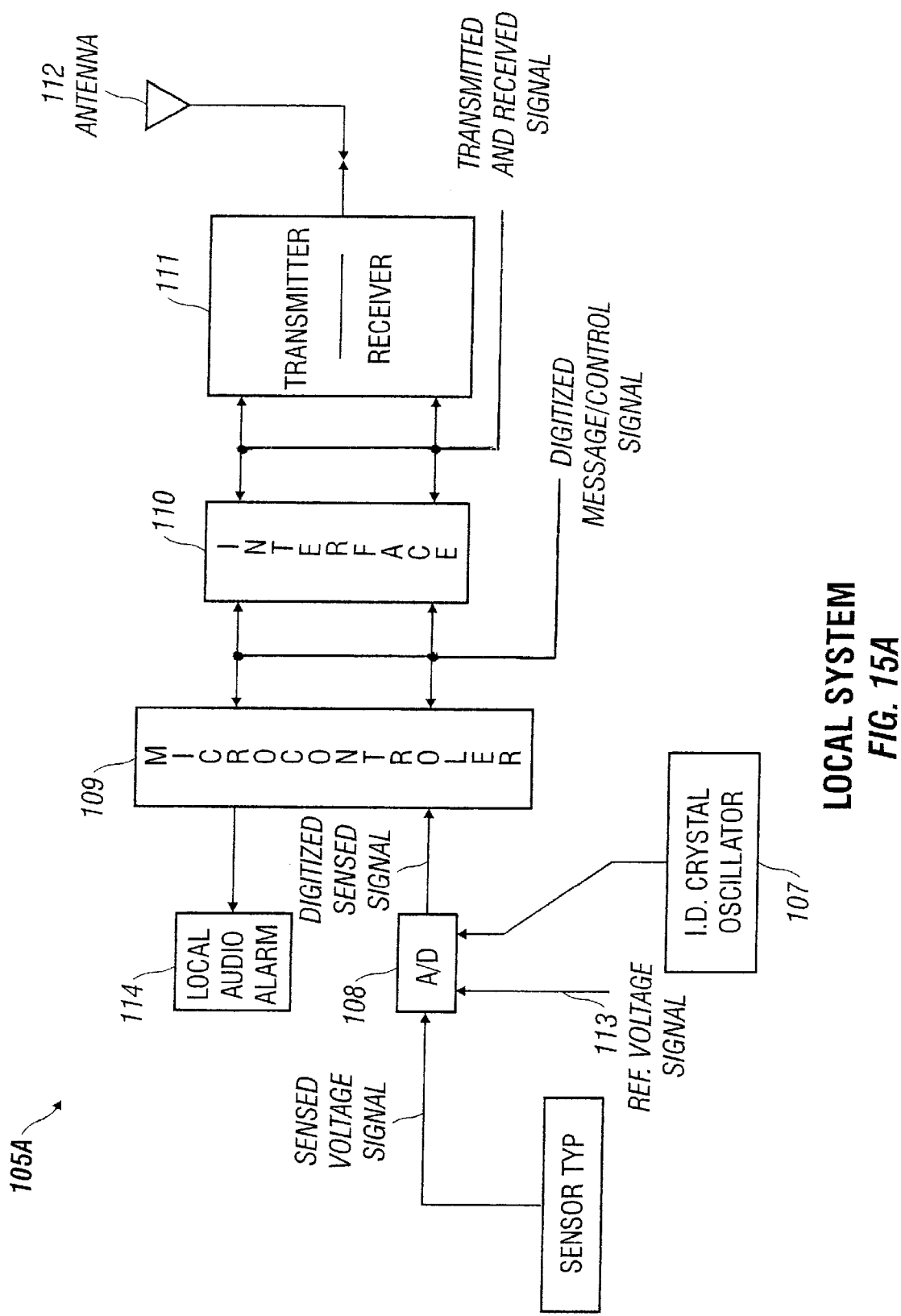
FIG. 15A is a schematic diagram of a communications network which can be incorporated with the garment of the invention as a means for transmitting to a remote base station, signals as to his physical condition, identity and location and for receiving signals from the base station.

In FIG. 15A, there is shown a schematic diagram of a communications network 105A which can be incorporated in a garment 10. When worn by a garment-wearer provided with sensor probes 102 and a crystal oscillator 107 which generates an electrical signal of unique frequency in response to motion, the system is adapted to process the signals and transmit the processed signals to a base station. The base station is provided with a communication system 105B as shown schematically in FIG. 15B, which system is adapted to receive the signals from the garment-wearer, process the signals including tile oscillator signal which identifies the garment-wearer, and also to transmit signals back to the garment-wearer as may be desirable or necessary.

Referring more particularly to FIG. 15A, it will therein be seen that sensor signals as from probes 102 and the signal from the crystal oscillator 107, are delivered to an analog-to-digital (A/D) converter 108. The digitized signals are then delivered to a microcontroller 109 for multiplexing and processing. The microcontroller 109 provided with appropriate interface circuitry 110, relays the signals to a low power FM transceiver 111 which transmits through an antenna 112 to its base station.

A reference voltage signal, corresponding to a normal range of signals representing physiological data, is delivered from an appropriate voltage source 113 to the A/D converter 108 where it is compared to the sensor signals. If the sensed data is out of normality, a local audio alarm 114 is activated.

Referring to FIG. 15B, it is to be seen that signals from the garment-wearer, are adapted to be received by an antenna 115 and a transmitter/receiver 116 and delivered to a microcontroller 118 via appropriate interface circuitry 117. The microcontroller 118, the delivers the de-multiplexed processed signals to a visual display 119 and data storage file 120. Should there be any alarming situation at the garment-wearer's location, as indicated by the processed signals, an activating signal is delivered from the microcontroller 118 to an alarm 121 which provides an audible or visual alarm signal as is desired to alert the base personnel of the situation. The base personnel can then send message signals, such as voice signals from a microphone (not shown) via an A/D converter 122, microcontroller 118, transceiver 116 and antenna 115 for purposes of alleviating the situation or informing the garment-wearer as may be appropriate, which base signals are received by the communications network 105A.

As previously stated, the garment 10 is also provided with bar code labels 55C, 55D which can include such important information as the garment wearer's identity, his medical history and germane medical information another person equipped with a hand-held bar code scanning wand could therefore scan the bar code labels on a "downed fire-fighter" or the like and communicate such information to a bar code reader and transmitter at a base station.

Figure 12:
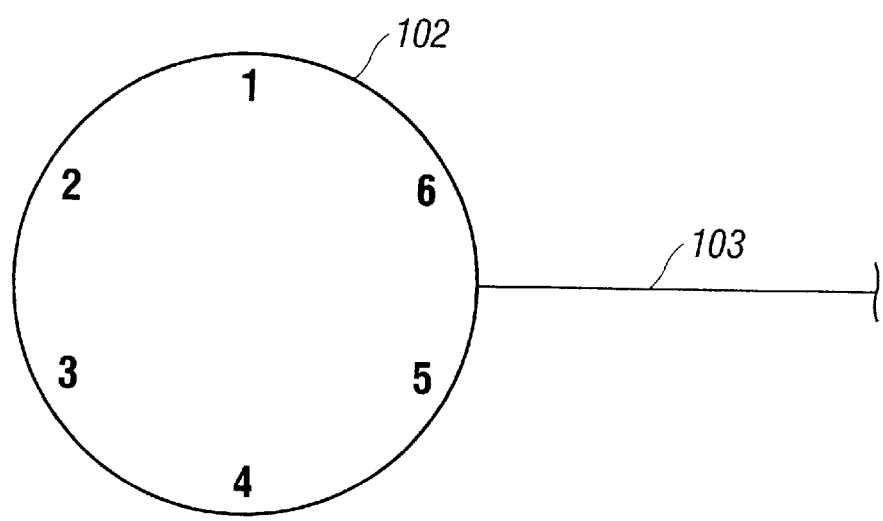
FIG. 12 is an enlarged plain view of a sensor probe which houses and supports a plurality of sensors for placement in a position adjacent to or in contact with the garment wearer's body.

In FIG. 12, there is shown a sensor probe 102 on which is mounted a plurality of sensors 1–6 for sensing vital physiological signs and which also houses the necessary transducers and a multiplexer. Sensors, well known in the art, can be provided to monitor pulse rate, blood pressure, blood oxygen saturation, intravascular volume status, body temperature, body surface moisture (humidity) or other important physiological signs. The multiplexed sensor signals are communicated by an electrical conductor 103 to an appropriate omnidirectional antenna 20D, such as an antenna disclosed in U.S. Pat. No. 5,714,937, which may be mounted on the garment belt as shown in FIG. 3. Also, an optimal second omnidirectional antenna mounted in a helmet as shown in U.S. Pat. No. 5,886,667 might also be employed. In general, the conductors 103 as shown in FIG. 8 will be routed from the sensor probes alongside the coolant conduits and from there to the antennas.

It is also to be appreciated that since the garment 10 is designed to control surface temperature of a particular body area, one of the sensor probes 102 may be provided in each of the body areas to be controlled and located, for example, at the ankles, the thighs, and the chests as shown in FIGS. 13 and 14.

It is also important that the surface body moisture and the humidity of a fire fighter be monitored. Accordingly, the protective garment 10 is preferably designed with a moisture barrier layer or lining made of a water-resistant material.

The water content in surrounding air is an important factor for determining the well-being of humans. The level of comfort is determined by a combination of two factors: relative humidity and ambient temperature. A hygrometer can be provided to measure humidity and to detect moisture contents. A sensor in a hygrometer must be provided which is selective to water, and its internal properties should be modulated by the water concentration.

Thus, in FIG. 3, a hygrometer 20E which measures both body moisture and the moisture/humidity under the outer suit that the fire fighter wears is shown mounted on the KEVLAR belt 19. The hygrometer 20E also includes a thermocouple located and operatively associated therewith in that it is necessary to monitor and record the temperature under the fire fighter's Nomex suit. This temperature monitoring is important because a fire fighter could be getting "cooked" and not be aware of the danger he is in until it is too late.

Also, it is to be appreciated that for some types of activities of the garment-wearer, it might be beneficial to the garment-wearer or a base station to know his location within a range of 10 to 20 feet. This can be achieved by placing on the garment-wearer a global positioning system (GPS) receiver which measures the distance to three satellites and by the principle of triangulation calculations the user's longitude, latitude and altitude within a range of a few feet. The received signals can also be forwarded through the communications system of FIG. 15A to a base station.

The garment 10 will also carry a rechargeable battery 20B of conventional type as an electrical power source for the various sensors and associated circuitry. As shown in FIG. 3 it is preferred the battery be mounted in the KEVLAR belt 19. In addition, it is to be noted that all of the electrical conductors carrying the various sensor output signals should preferably couple their signals to the signal conditioner and multiplexer/microprocessor as shown in FIG. 15 in preparation for transmission to a monitoring base.

One of the myriad novelties of this cooling garment is that the design lends itself to functioning with an outer shell covering such as coveralls. The materials of the outer covering can be those of Nomex, KEVLAR, Pbi, cotton and the like. In this particular case, the inner garment 10 set forth in FIG. 1 is stitched or fastened to the outer shell covering via snaps, Velcro zippers, or the like.

This particular design is important in that it will allow firefighters to walk around comfortably and freely in the garment as they would while wearing their cotton shirt and cotton trousers/khaki pants. In the event the firefighters have to answer an alarm, all is lacking is that they put their cooling holster (with other innovations included) about them and dress themselves as would beforehand.

In FIGS. 16A and 16B, there is shown an embodiment 10A of the invention wherein the garment 10A is shown as it is worn beneath a covering garment 125. For purposes of illustration only half of each garment 10A and 125 is shown. A Velcro patch 126 is shown affixed to the exterior of the outside portion of the garment 10A in a position to fasten with a cooperating Velcro patch (not shown) on the interior surface of the ankle portion of the covering garment 125. Other cooperating Velcro patches may be located at other locations on the two garments. In place of Velcro, however, the garments might be fastened by other suitable means or left unfastened with respect to one another in certain applications and conditions.

The garment 10A is also shown provided with a holster-like pocket 130 which is suspended on a KEVLAR belt 19A. The holster pocket 130 may be used as a substitute for the many container pockets 21 as are provided with the belt 19 shown in FIG. 3 and it may carry all the coolant canisters, the heat exchanger, the fan battery and filter shown in FIGS. 4, 5A and 5B. In addition the motion detector, hygrometer, electronic circuitry and rechargeable battery might also be carried therein.

It is to be appreciated that the Korotkoff Method of the measurement of the blood pressure which is widely used is usually done with a sphygmomanometer, a device having an inflatable cuff connect to a measuring device, often with a clear tube containing mercury. The cuff is placed around a limb and inflated until it compresses an artery to stop the flow of blood.

This temporarily shuts off the blood flow of the artery, and mercury rises in the tube. As the cuff is slowly deflated, mercury drops in the tube. With a stethoscope, the operator listens for the flow of blood to begin, indicating pressure in the cuff is just below the pressure of the artery. Such a device impedes and temporarily stops blood flow and is quite uncomfortable and furthermore, a sphygmomanometer does not give an on-going continuous reading of one's blood pressure.

Recent innovations to measure and monitor blood pressure have made use of a variety of sensors. Recent developments in tonometry include the development of non-invasive tonometry sensors that monitor the blood pressure waveform as a function of tissue stress and the tissue itself, such as is disclosed in U.S. Pat. No. 5,158,091. A problem arises in that it is necessary that the tissue stress sensor be maintained in controlled context with the overlying tissue such that unnecessary relative movements between the tissue (i.e., wrists) and the sensor do not introduce undesirable error or artifacts into the blood pressure measurement.

The sensor of choice to monitor and measure blood pressure and body chemistry is the piezoelectric sensor. Piezoelectricity is a reversible relationship between mechanical and electrostatic stress exhibited by certain crystals which lack a center of symmetry. For example, when pressure is applied to a piezoelectric crystal such as quartz, positive and negative electric charges appear on opposite crystal faces. Replacing pressure with tension, reverses the sign of the electrical charges. Piezoelectric materials are used as sensors because they are sensitive to very slight changes in pressure and provide an electrical output which can be easily amplified for display.

U.S. Pat. No. 5,033,471 discloses a means for measuring blood pressure, without use of a cuff, and suggests possible use of a piezoelectric sensor for detecting a pulse wave. However, a pump for applying pressure is still required.

Other materials than crystals are known which demonstrate piezoelectric properties, or can be manipulated to demonstrate such properties. Such materials are used in sonic sensors as disclosed in U.S. Pat. No. 4,578,613 which discloses an electro-acoustic device with two sheets of foil stretched about a curve in perpendicular directions in which a first foil has been permanently altered to provide directional piezoelectric actions on a curved surface and a second foil measures perpendicular strain. A suggested use is for amplifying of acoustic signals. The piezoelectric material is over-stretched, pre-charged polymeric film.

There is a need for firefighters and industrial workers (in the field) to have their blood pressure and body chemistry monitored continuously. Such information acquired on those and other garment-wearers can add to their overall health and morale.

The blood pressure monitoring device of choice for this cooling garment is described in U.S. Pat. No. 5,553,503. This device comprises a flexible piezoelectric material covering the opening of a changer which contains an electrically non-conductive elastomeric material and a lower outer layer of metal, such as chromium, which is adapted to be disinfected and placed against the skin adjacent an artery for measuring blood pressure. This blood pressure monitoring device is ideal for an array of reasons: first, there is no shunting of arterial blood. In the case of firefighters and industrial workers, that is important in that blood shunting in said cases can attribute to fainting and thus injury within the work place.

Other advantages are that it provides accurate continuous blood pressure monitoring, is non-invasive, i.e. surgical insertion of a sensor is not required, the circuitry of the system is suitable for miniaturization, and it can be used for measurement of continuous pressure and pressure fluctuation in a flexible environment. The circuitry in its entirely is disclosed i the U.S. Pat. No. 5,593,503 which is incorporated herein by reference.

It is to be appreciated that the foregoing description of the invention has been presented for purposes of illustration and explanation and is not intended to limit the invention to the precise form disclosed. For example, the conduit system may be comprised of a greater or lesser number of component distribution systems than herein described. Furthermore, while the cooling ventilating system for the protective garment of the invention has been disclosed as an open system wherein coolant fluid can be exhausted past the fittings at the body extremities such as wrist cuffs or by a pressure-actuated exhaust valve fitted in an opening in the garment material, the ventilating system could also be a closed system wherein coolant media after distribution through the garment interior is re-introduced to the filter inlet. It is to be appreciated therefore that changes may be made by those skilled in the art without departing from the spirit of the invention.

What is claimed is:

1. A body protective garment having portions shaped to enclose at least the torso of a wearer, said garment being comprised of a body-enveloping material with an inlet port provided in said garment material;

means for supplying a dehumidified coolant medium to said inlet port, said means for supplying a coolant medium being fastened to the garment exterior for distributing the dehumidified coolant medium to flow over the various body parts of the wearer, said means for distributing the coolant medium comprising a system of flexible conduits fixed to the interior surface of the garment and including component distribution systems leading to the various parts of the wearer's body, and the interior surface of the garment being provided with a system of grooves wherein said grooves open inward towards the body surface of the garment wearer, each said conduit being provided with holes along its length for communicating the coolant medium to the system of grooves in the garment and distributing the coolant over the surface of the wearer's body; and valve means installed in each component conduit distribution system and automatically responsive to the temperature of the coolant medium when distributed over a particular body area associated with said component conduit distribution system to control the flow of coolant medium so as to maintain the surface temperature of the wearer's particular body area in a prescribed temperature range.

2. A body protective garment as set forth in claim 1 wherein said valve means in each component conduit distribution system is operative to maintain the surface temperature of the wearer's particular body area in the temperature range at 72° to 75°.

3. A body protective garment as set forth in claim 1 wherein said means for supplying a coolant medium comprises a plurality of canisters carried about the waist of the garment and containing pressurized coolant medium, said canisters each having an outlet being connected by a manifold conduit to said inlet; and a manually operable valve installed in said manifold conduit and operable by the garment wearer for controlling communication of said coolant medium to said inlet and said system of flexible conduits.

4. A body protective garment as set forth in claim 2 wherein each conduit in said system of conduits is provided with holes along its length wherein said holes are of increasing diameter proportional to the distance of each said hole from said inlet and said holes are in direct communication with the grooves in the garment's interior surface.

5. A body protective garment as set forth in claim 3 wherein the outlet of said manually operable valve is connected to the inlet of a heat exchanger for warming the coolant medium, said heat exchanger having a thermostatic valve installed in its outlet end and a dehumidifying filter having an inlet connected to the outlet end of the heat exchanger; and said filter having an outlet connected to the inlet port in said garment material, said thermostatic valve being operable to open and admit coolant medium to said system of flexible conduits when the temperature of the coolant medium at the filter outlet reaches approximately 76° F.

6. A body protective garment as set forth in claim 5 wherein said filter contains moisture removing material of anhydrous calcium sulfate which changes color as water is filtered out of the coolant medium and is absorbed therein.

7. A body protective garment as set forth in claim 6 wherein said filter is adapted to remove moisture, contaminants and particles from the coolant medium and includes a tubular housing with a transparent window whereby a wearer of the suit can observe a color change of the anhydrous calcium sulfate.

8. A body protective garment as set forth in claim 1 wherein said garment is comprised of a body enveloping material which is elastic and impervious to gaseous fluids.

9. A body protective garment as set forth in claim 3 wherein said plurality of pressurized canisters are carried about the waist of the garment on a KEVLAR belt provided with a plurality of pockets of KEVLAR material for receiving said canisters and providing a covering therefor as a protection for the garment wearer.

10. A body protective garment as set forth in claim 3 further including pressure relief means comprising a pressure relief valve coupled to the outlets of said canisters and operative to achieve coolant pressure in said canisters when the pressure in said canisters reaches a predetermined level.

11. A body protective garment as set forth in claim 1 wherein said garment is provided with zippered openings on the front and rear of said garment which allow for easy donning and removal of the garment and permit the garment wearer to eliminate body excretions.

12. A body protective garment as set forth in claim 11 wherein said zippered openings are provided by zippers made of KEVLAR.

13. A body protective garment constructed and shaped to enclose at least the torso of a wearer, said garment being comprised of a body-enveloping material and having an inlet port provided in said garment material;

means for supplying a dehumidified coolant medium to said inlet, said means for supplying coolant medium being fastened to the garment exterior and including means for distributing the dehumidified coolant medium to flow over the various body parts of the wearer, said means for distributing coolant medium comprising a system of flexible conduits fixed to the interior surface of the garment and including component distribution systems leading to the various parts of the wearer's body, each said conduit in said component distribution systems being provided with holes along its length for communicating the coolant medium to the interior of the garment and distributing the coolant over the surface of the wearer's body; and temperature controller means installed in said system of flexible conduits and automatically responsive to the temperature of coolant medium when distributed over a particular body area to control the flow of coolant medium so as to maintain the surface temperature of the wearer's particular body area in a prescribed temperature range.

14. A body protective garment as set forth in claim 13 wherein said garment is comprised of a body-enveloping material which is elastic and durable.

15. A body protective garment as set forth in claim 13 wherein said garment includes portions constructed and shaped to enclose the arms, legs and torso of a wearer of the garment.

16. A body protective garment as set forth in claim 13 wherein said temperature controller means includes thermocouples located adjacent various body parts of the garment wearer and computer microprocessor means responsive to said thermocouples for constantly monitoring the surface body temperature of said various body parts.

17. A body protective garment as set forth in claim 13 wherein said temperature controller means includes valve means installed in each said component distribution system, and means for sensing the surface body temperature of the various body parts of the garment wearer and means responsive to the sensed temperatures for regulating said valve means and controlling the amount of coolant that is distributed throughout said garment.

18. A body protective garment as set forth in claim 13 further including means for sensing and monitoring physiological life signs of the garment wearer.

19. A body protective garment as set forth in claim 18 wherein said physiological life signs include anyone of the group of physiological life signs comprising pulse rate, blood pressure, respiration rate, blood oxygen saturation, body surface moisture and humidity, intravascular volume status, and core body temperature.

20. A body protective garment as set forth in claim 13 further including means for detecting motion and non-motion of the garment wearer and generating and transmitting indications of the garment wearer's motion activity to a monitoring base station.

21. A body protective garment as set forth in claim 13 further comprising means including a crystal resonator for generating an electrical signal of specified frequency assigned to the garment wearer, and means for transmitting said crystal resonator signal to a monitoring base station whereby the garment wearer can be readily identified.

22. A body protective garment as set forth in claim 13 wherein said garment is affixed to an outer shell garment by fastener means selected from the group comprising zippers, snap fasteners, Velcro fasteners, buttons, and stitching, and said outer shell garment is in the form of said coveralls made of material selected from the group comprising Nomex material, cotton, KEVLAR, Pbi and any combination thereof.

23. A body protective garment as set forth in claim 16 further including means for sensing and monitoring physiological life signs of the garment-wearer and generating signals representative thereof, and electrical signal communication means for transmitting said generated signals to a remote base station.

24. A body protective garment as set forth in claim 23 further including:

thermocouple means for sensing and detecting abnormally high temperature between said protective garment and an outer shell garment, and electrical signal communication means for transmitting said abnormally high temperature signal to a monitoring base station.

25. A body protective garment as set forth in claim 13 wherein said garment has affixed to it a bar code label and a bar code communications system wherein said garment utilizes said bar code system to record and retrieve inventory information and such vital information as the garment-wearer's german medical history so as to provide information that will assist in identifying the garment-wearer in case of unconsciousness, and in recalling information in various presentation formats at display terminals and at printer devices;

a portable hand-held bar code reading device that communicates with the communication system and employs a non-ohmic electrical contact between the bar-code attached to the garment and a reader in an associated station for transferring data to and from the bar-code label.

26. A body protective garment as set forth in claim 23 wherein said supply of coolant medium comprises a plurality of canisters, and said garment is provided with a belt having a holster pocket suspended therefrom for carrying said canisters, and microcontroller means therein.

27. A body protective garment as set forth in claim 23 wherein said garment has a global positioning system receiver mounted on said garment for receiving signals from global positioning satellites and adapted to calculate and provide signal indications as to its location from said satellite signals, said receiver being connected to said communication system for transmitting signals of its location to a remote base station.

* * * * *